(12) United States Patent
Van Der Puy et al.

(10) Patent No.: US 6,300,532 B1
(45) Date of Patent: Oct. 9, 2001

(54) PROCESS FOR ADDITION OF HALOALKANES TO ALKENES CATALYZED BY AN ORGANOPHOSPHITE COMPOUND

(75) Inventors: Michael Van Der Puy; Timothy Rech Demmin, both of Erie County, NY (US)

(73) Assignee: AlliedSignal Inc., Morris Township, NJ (US)

( * ) Notice: Subject to any disclaimer, the term of this patent is extended or adjusted under 35 U.S.C. 154(b) by 0 days.

(21) Appl. No.: 09/212,037

(22) Filed: Dec. 15, 1998

(51) Int. Cl.[7] ............................ C07C 21/18; C07C 41/00; C07C 69/63
(52) U.S. Cl. .......................... 570/172; 570/144; 570/191; 570/257; 568/681; 568/684; 560/226; 560/227
(58) Field of Search ..................................... 570/257, 172, 570/144, 191; 568/681, 684; 560/226, 227

(56) References Cited

U.S. PATENT DOCUMENTS 4,605,802   8/1986   Astrologes .

OTHER PUBLICATIONS

Chemical Abstracts, vol. 073, No. 17, Oct. 26, 1970 (Oct. 26, 1970) Columbus, Ohio, US; abstract No. 087347, Asahara T et al. "Reaction of Ethylene with 1,1,1,3—tetrachloropropane" XP002136357 abstract & Seisan–Kenkyu (Sekeai); 1970; vol. 22 (4); pp. 169–171, Japan.

Huang W. et al "Reactions of perfluoroalkyl iodides with alkenes initiated by organophosphine and related compounds" J. Fluorine Chem. (JFLCAR. 00221139); 1990; pp. 133–140, XP002136356 Acad. Sin.; Shanghai Inst. Org. Chem.; cited in the application p. 133; table 2.

Burton et al., "Copper Chloride–Ethanolamine Catalyzed Addition of Polyhaloalkanes to 1–Octene[1]," Journal of Organic Chemistry, 1970, pp. 1339–1342.

Asscher et al., "Chlorine Activation by Redox Transfer. Part II. The Addition of Carbon Tetrachloride to Olefins," Journal of the Chemical Society, 1963, pp. 1887–1895.

T. Fuchikami et al., "Transitiion–Metal Complex Catalyzed Polyflouroalkylation. I. Facile Addition of Polyfluoroalkyl halides to Carbon–Carbon Multiple Bonds," Tetrahedron Letters, vol. 25, No. 3, 1984, pp. 303–306.

T. Ishihara et al., "New Efficient Palladium–Catalyzed Perfluoroalkylation of Carbon–Carbon Multiple Bonds with F–Alkyl Iodides. An Expedient Route to F–Alkylated Alkyl and Alkenyl Iodides," Chemistry Letters, 1986, pp. 1895–1896.

W.Y. Huang et al., "Reaction of Perfluoroalkyl Iodides With Alkenes Initiated by Organophosphine and Related Compounds," Journal of Fluorine Chemistry, 50, 1990, pp. 133–140.

A. Feiring, "Reaction of Perfluoroalkyl Iodides with Electron Donor Nucleophiles," J. Org. Chem 50(18) 3269–3272 (1985).

Van Der Puy, et al., "Preparation, fluorination and synthetic utility of a CFC–olefin adduct", Journal of Fluorine Chemistry, 76 (1996) pp. 49–54.

N. Brace, "Syntheses with F–Alkyl Radicals from F–Alkyl Iodides: Amine and Amine Salt Induced Addition toAlkene," J. Org. Chemistry, 44(2) (1979) 212–217.

C.M. Hu et al, "Addition of 1,1,2–Trichloro–1,2,2–Trifluoroethane (F113) to Aklenes and Alkynes Initiated by a Redox System", Tetrahedron Letters, vol. 31, No. 9, pp. 1307–1308 (1990).

J.D. Park, et al., "Free–Radical Catalyzed Addition of Unsaturated Alcohols to Perhaloalkanes," J. Org. Chem, vol. 26, Jun. 1961, pp. 2089–2095.

J. Balague, et al., "Synthesis of Fluorinated Telomers. Part 1. Telomerization of vinylidene fluoride with perfluoroalkyl iodides", Journal of Fluorine Chemistry 70 (1995) pp. 215–223.

M. Kotora, et al., "Copper–Catalyzed Addition of Perfluoroalkyl Iodides to Unsaturated Alcohols and Transmformation of the Additon Products", Journal of Fluorine Chemistry, 68 (1994) pp. 49–56.

H. Nair et al., "A New Synthetic Route to Perfluoroalkylidene–α–ω–Bisphosphonates", Tetrahedron Letters, vol. 36, No. 6041 (1995) pp. 347–350.

N. Brace, "Some Approaches to the Synthesis of Fluorinated Alcohols and Esters. II. Use of F–Alkyl Iodides for the Synthesis of F–Alkyl Alkanols", J. Fluorine Chemistry, vol. 20 (1983) pp. 313–327.

*Primary Examiner*—Alan Siegel
(74) *Attorney, Agent, or Firm*—Colleen D. Szuch

(57) ABSTRACT

A process for catalytic addition of haloalkanes to alkenes involving the step of reacting the haloalkane with the alkene in the presence of a catalyst. The catalyst is an organophosphite compound represented by the following formula: $P(OR_a)(OR_b)(OR_c)$, where $R_a$, $R_b$, and $R_c$ are each an alkyl group or an aralkyl group. The haloalkane is as follows: (i) $CR^1R^2R^3R^4$, wherein (a) each of $R^1$, $R^2$, $R^3$ and $R^4$ is selected from the group consisting of a chlorine atom, a bromine atom or an iodine atom; or (b) $R^1$ is selected from the group consisting of a linear alkyl group; a halosubstituted linear alkyl group; an aralkyl group; an aralkyl group substituted with at least one of a halogen atom on the alkyl portion thereof or a halogen atom, alkyl group, alkoxy group or $—CO_2R^{10}$ wherein $R^{10}$ is a $C_1$–$C_4$ alkyl group on the aryl portion thereof; an aryl group and an aryl group substituted with at least one of a chlorine atom, a fluorine atom, an alkoxy group or a $—CO_2R^{11}$ group, wherein $R^{11}$ is a $C_1$–$C_4$ alkyl group; and $R^2$, $R^3$ and $R^4$ are as follows: $R^2$ is an iodine atom and $R^3$ and $R^4$ are each a halogen atom except $R^3$ and $R^4$ are not each a bromine atom or $R^2$ and $R^3$ are each a bromine atom and $R^4$ is a halogen atom. The catalyzed addition of the haloalkane to the alkene proceeds without any other components present in an excess amount, by weight, of the combined amount of the haloalkane, alkene and organophosphite catalyst compound.

14 Claims, No Drawings

PROCESS FOR ADDITION OF HALOALKANES TO ALKENES CATALYZED BY AN ORGANOPHOSPHITE COMPOUND

FIELD OF THE INVENTION

The present invention relates to a process for the catalytic addition of haloalkanes to alkenes in the presence of an organophosphite catalyst compound.

BACKGROUND OF THE INVENTION

U.S. Pat. No. 4,605,802 is directed to the addition of a haloalkane (carbon tetrachloride) to an alkene (ethylene) in the presence of a phosphite ester complexing agent (such as triethylphosphite) and an iron-containing catalyst material (such as powdered iron or iron chloride) to produce the haloalkane addition product (1,1,1,3-tetrachloropropane). This addition reaction occurs in the absence of solvent. The addition of 1,1,1-trichlorotrifluoroethane to ethylene using an iron/triethylphosphite co-catalyst system in the absence of a solvent was also reported in the *Journal of Fluorine Chemistry*, 76 (1996) 49–54.

The addition of polyhaloalkanes to 1-octene by an oxidation-reduction addition in the presence of a copper chloride catalyst was reported in Burton et al., *Journal of Organic Chemistry* (1970), pages 1339 to 1342. A similar type of oxidation-reduction addition was discussed earlier by Asscher et al in an article in the *Journal of the Chemical Society* (1963) at pages 1887 to 1895. Asscher et al. is directed to the addition of carbon tetrachloride to alkenes in the presence of a copper-containing or iron-containing catalyst. Asscher et al. reported that the use of the metal-containing catalyst effectively minimizes telomerization reactions, thereby producing a greater yield of the 1:1 addition adduct.

Others have generally taught the use of metal-containing catalysts to add haloalkanes across a carbon-carbon multiple bond. For example, T. Asahara et al., in two articles in volume 74 of Kogyo Kagaku Zasshi (1971), at pages 703 to 705 and 2288 to 2290, discuss the reaction of carbon tetrachloride with ethylene in the presence of a phosphite ester complexing agent and metal salts, particularly, iron chloride, to effect telomerization. The reactions proceed to various degrees, producing 1,1,1,3-tetrachloropropane along with relatively large amounts of higher telomers, as follows:

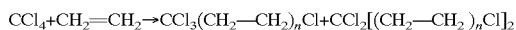

wherein n is primarily 1 with significant amounts of n as 2 and 3.

T. Fuchikami et al., an article in *Tetrahedron Letters*, Vol. 25, No. 3 (1984), at pages 303 to 306, is directed to the use of a transition-metal complex catalyst in the addition of polyfluoroalkyl halides to carbon-carbon multiple bonds.

T. Ishihara et aL, an article in *Chemistry Letters* (1986), at pages 1895–1896, is directed to the perfluoroalkylation of alkynes with perfluoroalkyl iodides in the presence of a palladium catalyst.

Still others have employed initiators such as amines or amine salts (Brace, *J. Org. Chem.*, 44(2) 212–217 (1979)) or arenesulfonate and alkanesulfinate salts (Feiring, *J. Org. Chem.* 50(18), 3269–3272 (1985)). Other prior art catalysts include $Fe(CO)catalyst)_5$, $Mn(CO)_{10}$, and $RuCl_2$.

In these prior art examples, the reaction mechanism is thought to involve radical or radical-type intermediates formed by single electron transfer (SET) processes. The metal component of the catalyst is typically in an electron rich low valence state and transfers a single electron to the haloalkane to initiate the transformation. In other examples, similar addition reactions have been brought about by thermolysis, photolysis, electrolysis, or free radical initiation, for example, using organic peroxides such as benzoyl peroxide. These alternate addition methods all involve radical species as intermediates.

Use of such metal catalysts, however, generally suffer from several drawbacks; e.g., they may be expensive, they may lead to unwanted by-product formation, they may require removal from the final product and they may require special environmental handling and disposal procedures that are nonhazardous to the environment.

An article in the *Journal of Fluorine Chemistry*, 50 (1990), W. Y. Huang et al., at pages 133–140, is directed to the use of phosphorus derivatives, including triethylphosphite, as catalysts in the presence of excess acetonitrile (i.e., present in an amount that exceeds the total amount of reactants and catalyst). The excess acetonitrile is said to be needed for successful addition of the perfluoroalkyl iodide to the alkene.

However, use of such additives (as in Huang et al) generally suffer from several drawbacks; e.g., the preferred excess component must be determined to maximize process performance, the productivity is lowered by the volume of the excess component carried through the process equipment, the excess component must be dry, and it may require removal in a separate step for recycle or disposal.

OBJECTS AND SUMMARY OF THE INVENTION

The present invention provides a process for the catalytic addition of haloalkanes (as defined below) to alkenes in the presence of a catalyst, wherein the catalyst is an organophosphite compound.

More specifically, the present invention provides a process for catalytic addition of a haloalkane to an alkene comprising the step of reacting the haloalkane with the alkene in the presence of a catalyst, wherein said catalyst consists of an organophosphite compound represented by the following formula: $P(OR_a)(OR_b)(OR_c)$, wherein $R_a$, $R_b$, and $R_c$ are each selected from the group consisting of an alkyl group and an aralkyl group; wherein said haloalkane is as follows:

(i) $CR^1R^2R^3R^4$, wherein (a) each of $R^1$, $R^2$, $R^3$ and $R^4$ is selected from the group consisting of a chlorine atom, a bromine atom or an iodine atom; or (b) $R^1$ is selected from the group consisting of a linear alkyl group; a halo-substituted linear alkyl group; an aralkyl group; an aralkyl group substituted with at least one of a halogen atom on the alkyl portion thereof or a halogen atom, alkyl group, alkoxy group or $—CO_2R^{10}$ wherein $R^{10}$ is a $C_1$–$C_4$ alkyl group on the aryl portion thereof; an aryl group and an aryl group substituted with at least one of a chlorine atom, a fluorine atom, an alkoxy group or a $—CO_2R^{11}$ group, wherein $R^{11}$ is a $C_1$–$C_4$ alkyl group; and $R^2$, $R^3$ and $R^4$ are as follows: $R^2$ is an iodine atom and $R^3$ and $R^4$ are each a halogen atom except $R^3$ and $R^4$ are not each a bromine atom or $R^2$ and $R^3$ are each a bromine atom and $R^4$ is a halogen atom;

(ii) $CR^5R^6R^7I$, wherein $R^5$ is a fluorine atom and $R^6$ and $R^7$ are each a halogen atom, except $R^6$ and $R^7$ are not each a bromine atom; or (iii) $CR^8R^9Br_2$, wherein $R^8$ is a fluorine atom and $R^9$ is a halogen atom;

and wherein the catalyzed addition of the haloalkane to the aikene proceeds without any other components present in an excess amount, by weight, of the combined amount of the haloalkane, alkene and organophosphite catalyst compound.

The present invention further provides a process for catalytic addition comprising adding a haloalkane to an alkene in the presence of an organophosphite catalyst compound, wherein said catalytic addition consists essentially of said haloalkane, alkene and organophosphite catalyst compound; said organophosphite catalyst compound consists of an organophosphite compound represented by the following formula: $P(OR_a)(OR_b)(OR_c)$, wherein $R_a$, $R_b$, and $R_c$ are each selected from the group consisting of an alkyl group and an aralkyl group; and said haloalkane is as follows:

(i) $CR^1R^2R^3R^4$, wherein (a) each of $R^1$, $R^2$, $R^3$ and $R^4$ is selected from the group consisting of a chlorine atom, a bromine atom or an iodine atom; or (b) $R^1$ is selected from the group consisting of a linear alkyl group; a halo-substituted linear alkyl group; an aralkyl group; an aralkyl group substituted with at least one of a halogen atom on the alkyl portion thereof or a halogen atom, alkyl group, alkoxy group or $-CO_2R^{10}$ wherein $R^{10}$ is a $C_1$–$C_4$ alkyl group on the aryl portion thereof, an aryl group and an aryl group substituted with at least one of a chlorine atom, a fluorine atom, an alkoxy group or a $-CO_2R^{11}$ group, wherein $R^{11}$ is a $C_1$–$C_4$ alkyl group; and $R^2$, $R^3$ and $R^4$ are as follows: $R^2$ is an iodine atom and $R^3$ and $R^4$ are each a halogen atom except $R^3$ and $R^4$ are not each a bromine atom or $R^2$ and $R^3$ are each a bromine atom and $R^4$ is a halogen atom;

(ii) $CR^5R^6R^7I$, wherein $R^5$ is a fluorine atom and $R^6$ and $R^7$ are each a halogen atom, except $R^6$ and $R^7$ are not each a bromine atom; or (iii) $CR^8R^9Br_2$, wherein $R^8$ is a fluorine atom and $R^9$ is a halogen atom.

The present invention also provides a process for catalytic addition comprising reacting a reaction mixture in the presence of a catalyst to form an addition product, wherein said reaction mixture consists essentially of a haloalkane, alkene and an organophosphite catalyst compound; said organophosphite catalyst compound consists of an organophosphite compound represented by the following formula: $P(OR_a)(OR_b)(OR_c)$, wherein $R_a$ $R_b$ and $R_c$ are each selected from the group consisting of an alkyl group and an aralkyl group; and said haloalkane is as follows:

(i) $CR^1R^2R^3R^4$, wherein (a) each of $R^1$, $R^2$, $R^3$ and $R^4$ is selected from the group consisting of a chlorine atom, a bromine atom or an iodine atom; or (b) $R^1$ is selected from the group consisting of a linear alkyl group; a halo-substituted linear alkyl group; an aralkyl group; an aralkyl group substituted with at least one of a halogen atom on the alkyl portion thereof or a halogen atom, alkyl group, alkoxy group or $-CO_2R^{10}$ wherein $R^{10}$ is a $C_1$–$C_4$ alkyl group on the aryl portion thereof; an aryl group and an aryl group substituted with at least one of a chlorine atom, a fluorine atom, an alkoxy group or a $-CO_2R^{11}$ group, wherein $R^{11}$ is a $C_1$–$C_4$ alkyl group; and $R^2$, $R^3$ and $R^4$ are as follows: $R^2$ is an iodine atom and $R^3$ and $R^4$ are each a halogen atom except $R^3$ and $R^4$ are not each a bromine atom or $R^2$ and $R^3$ are each a bromine atom and $R^4$ is a halogen atom;

(ii) $CR^5R^6R^7I$, wherein $R^5$ is a fluorine atom and $R^6$ and $R^7$ are each a halogen atom, except $R^6$ and $R^7$ are not each a bromine atom; or (iii) $CR^8R^9Br_2$, wherein $R^8$ is a fluorine atom and $R^9$ is a halogen atom.

The present invention provides an improved catalyst system that permits the addition of haloalkanes (as defined herein) to alkenes to proceed with high yield, high selectivity and high efficiency without the common drawbacks generally associated with the use of components present in excess (so as to serve as a reaction medium) and metal catalysts (such as copper, iron and other metal species).

DETAILED DESCRIPTION OF THE INVENTION

The haloalkane used in the process of this invention is defined as follows: (i) $CR^1R^2R^3R^4$, wherein (a) each of $R^1$, $R^2$, $R^3$ and $R^4$ is selected from the group consisting of a chlorine atom, a bromine atom or an iodine atom, or (b) $R^1$ is selected from the group consisting of a linear alkyl group; a halo-substituted linear alkyl group; an aralkyl group; an aralkyl group substituted with at least one of a halogen atom on the alkyl portion thereof or a halogen atom, alkyl group, alkoxy group or $-CO_2R^{10}$ wherein $R^{10}$ is a $C_1$–$C_4$ alkyl group on the aryl portion thereof; an aryl group; and an aryl group substituted with at least one of a chlorine atom, a fluorine atom, an alkoxy group or a $-CO_2R^{11}$ group, wherein $R^{11}$ is a $C_1$–$C_4$ alkyl group; and $R^2$, $R^3$ and $R^4$ are as follows: $R^2$ is an iodine atom and $R^3$ and $R^4$ are each a halogen atom except $R^3$ and $R^4$ are not each a bromine atom or $R^2$ and $R^3$ are each a bromine atom and $R^4$ is a halogen atom; (ii) $CR^5R^6R^7I$, wherein $R^5$ is a fluorine atom and $R^6$ and $R^7$ are each a halogen atom except $R^6$ and $R^7$ are not each a bromine atom; or (iii) $CR^8R^9Br_2$, wherein $R^8$ is a fluorine atom and $R^9$ is a halogen atom.

The linear alkyl groups representing $R^1$ include methyl, ethyl, n-propyl and n-butyl groups. The halo-substituted linear alkyl group is a linear alkyl group containing one or more halogen atoms; e.g., a perfluoromethyl group and perfluoroethyl group. An example of the akyl group is $C_6H_5CH_2-$. The alkyl portion of the substituted aralkyl group may be substituted with one or more halogen atoms; e.g., $C_6H_5CF_2-$. An example of the aryl group is a phenyl group.

Specific examples of the haloalkane of the invention include $CCl_4$, $CF_2Br_2$, $CF_3I$, $CF_3CCl_2I$, $CF_3CFBrI$, $C_2F_5I$, $CHF_2CF_2I$, and $C_6H_5CF_2CF_2I$.

Any reactive alkene can be used in the present invention, preferably, terminal alkenes. More specific examples include ethylene, propylene, 1-butylene and vinyl halides such as vinyl fluoride ($CH_2CHF$) and vinylidene fluoride ($CH_2CF_2$).

The organophosphite compound catalyst of the invention is represented by the following formula: $P(OR_a)(OR_b)(OR_c)$, where $R_a$, $R_b$, and $R_c$ are each selected from the group consisting of an alkyl group and an aralkyl group. Examples include trialkylphosphite compounds and triaralkylphosphite compounds. The alkyl group of $R_a$, $R_b$, and $R_c$ may be a linear or branched alkyl group containing 1–10 carbon atoms optionally containing at least one of a nitrogen atom, oxygen atom, halogen atom, phosphorus atom or sulfur atom. Examples include a methyl group, ethyl group, n-propyl group, isopropyl group, n-butyl group, isobutyl group, or t-butyl group. A specific example of such a trialkylphosphite compound is triethylphosphite. Specific examples of a triaralkylphosphite compound are tribenzylphosphite and tri-p-methylbenzylphosphite. No metal-based coatalyst (such as a copper or iron co-catalyst) is required by this invention.

Thus, for example, a haloalkane (e.g., a perfluoroalkyl iodide such as $C_2F_5I$ (perfluoroethyl iodide)) is reacted with an alkene (e.g., $CH_2=CHF$ (vinyl fluoride)) to form the addition product (e.g., $C_2F_5CH_2CHFI$), in which an organophosphite compound (e.g., a phosphite ester such as triethylphosphite $((EtO)_3P)$) is employed as a catalyst for the addition reaction. Other exemplary reactions include the addition of perfluoroethyl iodide to ethylene and the addition of carbon tetrachloride to ethylene.

The catalyzed addition of the haloalkane to the alkene proceeds without requiring that any other components (i.e., other than the haloalkane, alkene and organophosphite catalyst compound) be present in an excess amount, by weight, of the combined amount of the haloalkane, alkene and organophosphite catalyst compound. For example, the catalyzed addition of the haloalkane to the alkene proceeds without the use of acetonitrile present in an excess amount, by weight, of the combined amount of the haloalkane, alkene and organophosphite catalyst compound. This, of course, includes reaction conditions where no components other than the haloalkane, alkene and organophosphite catalyst compound are present during the reaction.

Generally, the reaction may be carried out at about 50° C. to about 180° C., preferably, about 80° C. to about 150° C., and more preferably, about 90° C. to about 130° C. The reaction can be performed at varying reaction pressures. It is well within the skill in the art to determine such pressures. For example, a reaction pressure of 75–130 psig may be employed.

The organophosphite catalyst compound can be used in small amounts, e.g., about 0.001 to 0.100 molar equivalents based on the amount of haloalkane, preferably, 0.005 to 0.05 molar equivalents based on the amount of haloalkane, and, most preferably, about 0.01 to 0.02 molar equivalents based on the amount of haloalkane.

In general, the organophosphite catalyst compound may be added to the reaction vessel at room temperature. After addition of the organophosphite catalyst compound, the reaction vessel may be cooled for a period of time (e.g., in dry-ice). Thereafter, the haloalkane may be introduced into the reaction vessel, which may then be cooled (e.g., 10 minutes in dry-ice). The reaction vessel may then be evacuated for a period of time to remove air from the reaction system and subsequently brought to room temperature. Simultaneously therewith, the reaction vessel may be pressurized with the volatile alkene and then heated to the desired reaction temperature. As the reaction proceeds the alkene is consumed and the pressure accordingly decreases.

The alkene may be introduced periodically in order to maintain the pressure within the desired range and permit the addition of sufficient alkene to ensure the required conversion of haloalkane to the desired product.

The resulting crude product mixture may then be purified by a suitable conventional purification method, e.g., fractional distillation. Unlike other processes in which a copper or iron (or other metal) species is the active catalyst, there is no need to separate or deactivate the metal species as a prerequisite for product isolation. Furthermore, no components present in excess (by weight) of the combined amount of the alkene, haloalkane and organophosphite catalyst compound are utilized. Thus, the effective productivity is enhanced and the need to remove and recover the excess components is avoided.

The present invention is now described in more detail by reference to the following examples, but it should be understood that the invention is not construed as being limited thereto. Unless otherwise indicated herein, all parts, percents, ratios and the like are by weight.

EXAMPLE 1

Triethylphosphite, 0.27 g (0.0014 mol), and perfluoroethyl iodide, 27.80 g (0.113 mol), were added to an evacuated 100 ml glass pressure reactor containing a magnetic stir bar, pressure gauge, and ball valve. The mixture was freeze-pump-thaw degassed. The stirred homogeneous mixture was heated to 90° C. in a circulating constant temperature oil bath. After 15 minutes (pressure stabilized at 55 psig), the reactor was briefly charged with ethylene gas to a pressure of 90 psig and then resealed. The reaction mixture was similarly charged with eight additional pulses of ethylene comprising a total of 7.60 g (0.271 mol). A true reaction time is estimated at $\approx 35$ hours. The resulting clear light amber liquid, 25.77 g, (90% conversion and 86% selectivity for the desired product by gc analysis) was fractionally distilled to give 1,1,1,2,2-pentafluoro-4-iodobutane, 22.00 g (0.080 mol), bp 98–100° C., 71% yield.

$^1H$ NMR: 2.66 (sym. 7 peak mult, 2 H), and 3.23 (distorted t, J=8.4 Hz, 2 H). $^{19}F$ NMR: −85.98 (s, 3F), and −119.55 (t,J=17 Hz,2F).

EXAMPLE 2

Following a procedure similar to Example 1, a solution of perfluoroethyl iodide, 30.50 g (0.124 mol), and triethylphosphite, 0.23 g (0 0014 mol), was charged to: $\approx 15$ psig with vinyl fluoride at ambient temperature. The stirred mixture was then heated at 90° C. reaching a pressure maximum of 110 psig. As the reaction progressed and the pressure decreased to $\approx 75$ psig the vinyl fluoride was recharged, as before, in nine sequential pulses over a period of 124 hours. A true reaction time is estimated at $\approx 35$ hours. NMR analyses indicated 87% conversion of the perfluoroethyl iodide. The crude product was a mixture of isomers 1,1,1,2,2,4-hexafluoro-4-iodobutane (desired isomer) and 1,1,1,2,2,3-hexafluoro-4-iodobutane in a 96:4 ratio. The clear, colorless product mixture was fractionally distilled to give 1,1,1,2,2,4-hexafluoro4-iodobutane, 29.44 g (contains 10% perfluoroethyl iodide and a trace of isomeric adduct), bp 99–103° C., 84% yield.

$^1H$ NMR: (major isomer) 3.0 and 3.3 (bm, 2 H), and 7.11 (ddd, J=50.8, 9.5 and 2.1 Hz, 1 H); (minor isomer) hidden. $^{19}F$ NMR: (major isomer) −86.1 (s), −116.8 (dm, J=270 Hz), −118.8 (dm, J=270 Hz), and −142.5 (m); (minor isomer) −83.3 (d, J=10.8 Hz), −123.7 (dd, J=283.3 and 7.8 Hz), −133.1 (dd, J=283.0 and 15.2 Hz), and −193.6 (m).

EXAMPLE 3

Following the procedure of Example 1, a mixture of carbon tetrachloride, 33.16 g (0.216 mol), and triethylphosphite, 0.39 g (0.0023 mol), was treated with ethylene in 3 sequential pulses to 75 psig at 120° C. over a period of 66 hours. The light yellow, slightly turbid crude mixture was fractionally distilled to give 25.02 g of recovered carbon tetrachloride (24.5% conversion) and 5.02 g of $CCl_3CH_2CH_2Cl$ (0.028 mol), b.p. 85–87° C./100 mm Hg, 52% yield. The $^1H$ NMR spectrum, gc/mass spectrum, and gc retention time of the product matched those of authentic material.

Comparative Example 1

By direct comparison to Example 2, a "standard" addition reaction was performed using copper chloride as catalyst in acetonitrile solution (see table below). A mixture of copper chloride, 10.0 g (0.10 mol), and acetonitrile, 650 g (15.8 mol), was introduced under a nitrogen atmosphere into an evacuated 2 gallon Hastelloy C® autoclave. The system was chilled to 0° C., re-evacuated and charged with perfluoroethyl iodide, 711 g (2.89 mol), and with vinyl fluoride, 147 g (3.18 mol). The mixture was heated at 185° C. for 24 hours, with a pressure maximum of 520 psig, dropping to 265 psig after 24 hours. GC analysis indicated 80% conversion with 95% selectivity (both isomers) and an isomer ratio of 93:7 (desired isomer predominating). The dark product mixture required multiple aqueous washings to remove most of the acetonitrile, and a final aqueous bisulfite wash to remove liberated iodine. The residual acetonitrile was removed by careful fractional distillation through a 3 foot jacketed column packed with glass helices. 1,1,1,2,2,4-hexafluoro-4-iodobutane was isolated in 40% yield.

The reaction pressure was too high for scale-up equipment. Two additional examples were performed using more solvent, more catalyst and staged introduction of vinyl fluoride at lower pressure and temperature:

| ID | mol ratios | | | | °C. | Pmax | Hrs | Estimated $C_2F_5I$ Conv | Comments |
|---|---|---|---|---|---|---|---|---|---|
| | $CH_3CN$ | VF* | CuCl | $C_2F_5I$ | | | | | |
| Standard | 4–5 | 1.1 | 0.03 | 1.0 | 185 | 520 | 24 | 80% | 1 charge of VF* |
| Lo Press #1 | 10 | 1.1 | 0.08 | 1.0 | 175 | 300 | 40 | 76% | 3 charges of VF* |
| Lo Press #2 | 6 | 1.1 | 0.05 | 1.0 | 155 | 270 | 133 | 85% | 3 charges of VF* |

*VF = Vinyl Fluoride
Note: for all three procedures:
Selectivity for addition product formation (i.e., both butane isomers) was constant at 95%; and
Isomer ratio = 93%:7% (See Example 2)

None of the results for the three attempts was acceptable for scale-up. The pressures were still too great, the quantity of solvent limited the output of adduct/volume of reactor and necessitated a laborious aqueous workup, generating large quantities of aqueous waste. In addition, the above described reaction mixture aggressively attacked the metal surface of the reactor.

Comparative Example 2

As an additional comparison, the procedure of Example 2 was followed except 0.174 g (0.003 mol) of iron powder was additionally present. After a similar time period as in Example 2 only 5 pulses of vinyl fluoride had been consumed, and gc analysis had indicated only ≈36% conversion of the perfluoroethyl iodide. The presence of iron powder slowed the rate of addition by ≈50% and required an additional step for filtration.

Comparative Example 3

As an additional comparison, the procedure of Example 2 was followed except 0.143 g (0.0014 mol) of copper chloride was additionally present. After 21 hours at 90° C. there was a pressure drop of only 3 psi (107→104 psig). GC analysis had indicated <2% conversion to product. The presence of CuCl slowed the rate of addition by a factor of 30–40 and required an additional step for filtration.

Comparative Example 4

The procedure of Example 3 was followed except 0.152 g (0.0027 mol) of iron powder and 0.020 g (0.1 mmol) of $FeCl_3$ were additionally present. After 5 hours gc analysis revealed 50% conversion to $CCl_3CH_2CH_2Cl$, which was formed in >90% selectivity. Although these results indicate a substantially higher rate of addition, the presence of $FeCl_3$, a strong Lewis acid, leads to unwanted side reactions during product isolation, such as product decomposition by dehydrochlorination and polymerization. Special precautions to deactivate the $FeCl_3$ are required, e.g., addition of tributylphosphate prior to distillation. Furthermore, the unconsumed iron powder must be filtered prior to distillation.

While the invention has been described in detail and with reference to specific embodiments thereof, it will be apparent to one skilled in the art that various changes and modifications can be made therein without departing from the spirit and scope thereof.

What is claimed is:

1. A process for catalytic addition of a haloalkane to an alkene comprising the step of reacting the haloalkane with the alkene in the presence of a catalyst, wherein said catalyst consists of an organophosphite compound represented by the following formula: $P(OR_a)(OR_b)(OR_c)$, wherein $R_a$, $R_b$, and $R_c$ are each selected from the group consisting of an alkyl group and an aralkyl group; wherein said haloalkane is as follows:

(i) $CR^1R^2R^3R^4$, wherein (a) each of $R^1$, $R^2$, $R^3$ and $R^4$ is selected from the group consisting of a chlorine atom, a bromine atom or an iodine atom; or (b) $R^1$ is selected from the group consisting of a linear alkyl group; a halo-substituted linear alkyl group; an aralkyl group; an aralkyl group substituted with at least one of a halogen atom on the alkyl portion thereof or a halogen atom, alkyl group, alkoxy group or —$CO_2R^{10}$ wherein $R^{10}$ is a $C_1$–$C_4$ alkyl group on the aryl portion thereof; an aryl group and an aryl group substituted with at least one of a chlorine atom, a fluorine atom, an alkoxy group or a —$CO_2R^{11}$ group, wherein $R^{11}$ is a $C_1$–$C_4$ alkyl group; and $R^2$, $R^3$ and $R^4$ are as follows: $R^2$ is an iodine atom and $R^3$ and $R^4$ are each a halogen atom except $R^3$ and $R^4$ are not each a bromine atom or $R^2$ and $R^3$ are each a bromine atom and $R^4$ is a halogen atom;

(ii) $CR^5R^6R^7I$, wherein $R^5$ is a fluorine atom and $R^6$ and $R^7$ are each a halogen atom, except $R^6$ and $R^7$ are not each a bromine atom; or (iii) $CR^8R^9Br_2$, wherein $R^8$ is a fluorine atom and $R^9$ is a halogen atom;

and wherein the catalyzed addition of the haloalkane to the alkene proceeds without any other components present in an excess amount, by weight, of the combined amount of the haloalkane, alkene and organophosphite catalyst compound.

2. The process of claim 1, wherein said organophosphite catalyst compound is a trialkylphosphite compound.

3. The process of claim 1, wherein said organophosphite catalyst compound is a triaralkylphosphite compound.

4. The process of claim 1, wherein said alkyl group representing each of $R_a R_b$, and $R_c$ is a linear or branched alkyl group containing 1–10 carbon atoms optionally containing at least one of a nitrogen atom, oxygen atom, halogen atom, phosphorus atom or sulfur atom.

5. The process of claim 1, wherein said alkyl group representing each of $R_a$, $R_b$, and $R_c$ is a methyl group, ethyl group, n-propyl group, isopropyl group, n-butyl group, isobutyl group, or t-butyl group.

6. The process of claim 1, wherein said organophosphite compound is triethylphosphite.

7. The process of claim 1, wherein said haloalkane is a perfluoroalkyl iodide and said alkene is a terminal alkene.

8. The process of claim 1, wherein said haloalkane is $CCl_4$ and the alkene is ethylene or a vinyl halide.

9. The process of claim 1, wherein said haloalkane is perfluoroethyl iodide, said alkene is vinyl fluoride or vinylidene fluoride and said organophosphite catalyst compound is triethylphosphite.

10. The process of claim 1, wherein said linear alkyl groups representing $R^1$ include methyl, ethyl, n-propyl and n-butyl groups.

11. The process of claim 1, wherein said halo-substituted linear alkyl group is a perfluoromethyl group or a perfluoroethyl group.

12. The process of claim 1, wherein said haloalkane is selected from the group consisting of $CCl_4$, $CF_2Br_2$, $CF_3I$, $CF_3CCl_2I$, $CF_3CFBrI$, $C_2F_5I$, $CHF_2CF_2I$, and $C_6H_5CF_2CF_2I$.

13. The process of claim 1, wherein said alkene is ethylene, propylene, 1-butylene, vinyl fluoride or vinylidene fluoride.

14. The process of claim 1, wherein said aralkyl group representing each of $R_a$, $R_b$, and $R_c$ is tribenzylphosphite or tri-p-methylbenzylphosphite.

* * * * *